United States Patent [19]

Herd et al.

[11] Patent Number: 5,041,629
[45] Date of Patent: Aug. 20, 1991

[54] BETA-PHENOXYETHYLAMINES AND THEIR USE FOR THE PREPARATION OF DYESTUFFS

[75] Inventors: Karl J. Herd; Wolfgang Harms, both of Odenthal, Fed. Rep. of Germany

[73] Assignee: Bayer Aktiengesellschaft, Leverkusen, Fed. Rep. of Germany

[21] Appl. No.: 396,175

[22] Filed: Aug. 21, 1989

[30] Foreign Application Priority Data

Aug. 23, 1988 [DE] Fed. Rep. of Germany ....... 3828493

[51] Int. Cl.$^5$ ............................................. C07C 309/13
[52] U.S. Cl. ..................................... 562/37; 562/40; 562/435; 562/437; 562/451; 562/453; 560/14; 544/75; 544/76
[58] Field of Search .................................... 562/37–40, 562/437, 435, 451, 453; 560/14

[56] References Cited

U.S. PATENT DOCUMENTS

| 3,883,523 | 5/1975 | Parton | 541/76 |
| 3,996,221 | 12/1976 | Leng et al. | 541/76 |
| 4,298,603 | 11/1981 | Chang et al. | 562/451 |
| 4,577,015 | 3/1986 | Jager et al. | 544/75 |
| 4,874,857 | 10/1989 | Harms | 544/75 |

FOREIGN PATENT DOCUMENTS

| 2302382 | 7/1973 | Fed. Rep. of Germany . |
| 2344781 | 3/1974 | Fed. Rep. of Germany. . |
| 3635312 | 9/1988 | Fed. Rep. of Germany ........ 562/37 |
| 1353604 | 5/1970 | United Kingdom . |
| 1559752 | 5/1978 | United Kingdom . |
| 2019872 | 11/1979 | United Kingdom . |

OTHER PUBLICATIONS

R. Clinton et al., J. Am. Chem. Soc., "Derivatives of 4-Amino-2-Hydroxybenzoic Acid," 79, pp. 2285–2289 (1957).
W. Foye, "Principles of Medicinal Chemistry," 2nd Ed., pp. 339–347, Lee & Febigen, Philadelphia (1981).
Chemical Abstracts, vol. 71, Sep. 15, 1969, No. 11.

Primary Examiner—Richard L. Raymond
Assistant Examiner—Mark W. Russell
Attorney, Agent, or Firm—Sprung, Horn, Kramer & Woods

[57] ABSTRACT

The preparation is described of compounds of the structure

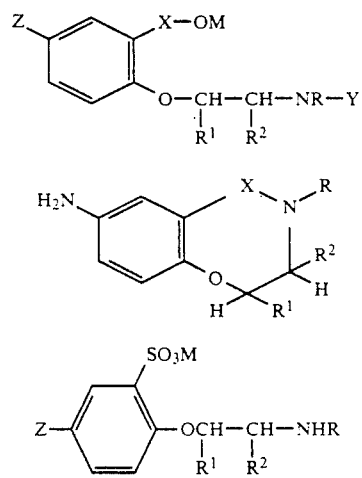

in which the substituents have the meanings indicated in the description. The compounds, which are in part new, are used as intermediate products for dyestuffs.

2 Claims, No Drawings

BETA-PHENOXYETHYLAMINES AND THEIR USE FOR THE PREPARATION OF DYESTUFFS

The present invention relates to β-phenoxyethylamines of the structure

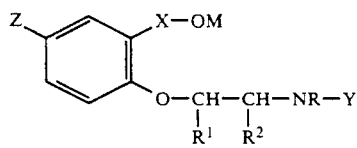  (1)

wherein
  Z = NH$_2$ or NO$_2$,
  M = H or an alkali metal cation, alkaline earth metal cation or ammonium cation,
  R = H or a C$_1$–C$_4$-alkyl, C$_2$–C$_4$-alkenyl or C$_2$–C$_4$-alkinyl radical each of which is optionally substituted (in particular by OH, Cl, Br, CN, CO$_2$H, CO$_2$CH$_3$, CO$_2$C$_2$H$_5$, CONH$_2$, CON(CH$_3$)$_2$, SO$_3$H, OSO$_3$H and C$_1$–C$_4$alkoxy) or a phenyl or benzyl radical each of which is optionally substituted (in particular by halogen, C$_1$–C$_4$-alkyl, CO$_2$H or SO$_3$H),
  R$^1$ and R$^2$ = independently of one another H, C$_1$–C$_4$-alkyl, phenyl or benzyl, it being also possible for R$^1$–R$^2$ to be a constituent of a cycloaliphatic radical,
  X = SO$_2$ or CO and
  Y = H or SO$_3$H,
  Y being SO$_3$M if X = SO$_2$, and
  Y being H if X = CO.

Preferred compounds (1) are those in which R$^1$ and R$^2$ = H and R = C$_1$–C$_4$-alkyl, CH$_2$CH$_2$OH, CH$_2$CO$_2$H or CH$_2$CH$_2$OSO$_3$H.

The invention also relates to a process for the preparation of the phenoxyethylamines (1) which is characterized in that 2-halogeno-5-nitrobenzenesulphonamides or 2-halogen-5-nitrobenzamides of the structures (2) (which can be prepared by known methods from 2-halogeno-5-nitrobenzenesulphonyl chloride or 2-halogeno-5-nitrobenzoyl chloride, respectively, and the corresponding amines)

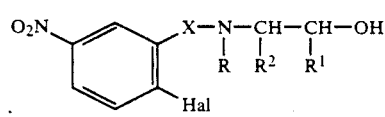

wherein
  X, R, R$^1$ and R$^2$ have the meaning mentioned under formula (1)
are cyclized at 80° to 110° C. in the presence of bases, in particular alkali metal hydroxides or alkali metal carbonates, such as sodium hydroxide solution, potassium hydroxide solution or sodium carbonate, to give 5,1,2-benzoxathiazepine 1,1-dioxides (X = SO$_2$) or 1,4-benzoxazepin-5-ones (X = CO), respectively, of the formula (3)

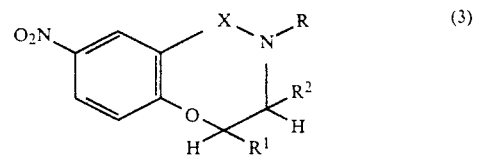  (3)

these benzosultams or benzolactams, respectively, are then reduced catalytically (for example hydrogen/catalyst), by means of metal/acid (for example iron/acetic acid) or by means of other reducing agents customary for aromatic nitro compounds to give amino compounds of the structure (4)

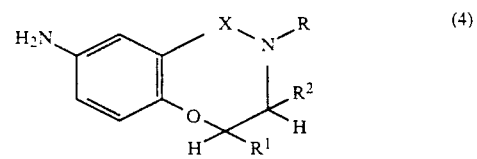  (4)

and the latter are finally hydrolyzed with ring opening. The hydrolysis of the benzosultams (X = SO$_2$) is preferably carried out in oleum at 60°–120° C. and affords, as single substances, the claimed amidosulphonic acids of the structure (5).

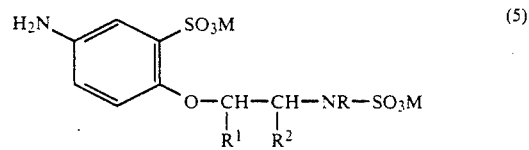  (5)

The corresponding alkali metal, alkaline earth metal or ammonium salts or betaines are accessible by subsequent neutralization.

The hydrolysis of the benzolactams (X = CO) is most suitably effected by means of dilute mineral acids, such as dilute hydrochloric acid or sulphuric acid, at reaction temperatures of 80°–110° C., and affords, if appropriate after neutralization, the claimed carboxy-substituted β-phenoxyethylamines of the structure (6) or hydrochlorides or hydrogensulphates thereof.

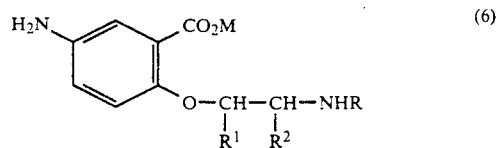  (6)

The invention also relates to a process for the preparation of the phenoxyethylamines of the structure (1) which is characterized in that benzosultams or benzolactams of the structure (3) are first hydrolyzed with ring-opening to give compounds of the formula (7) or (8), respectively,

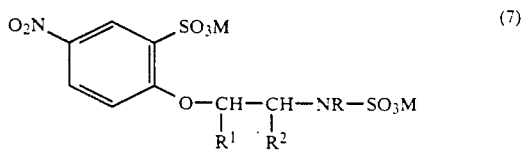  (7)

-continued

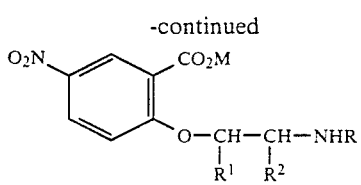

benzosultams (3, X=SO₂) being preferably hydrolyzed at 60° to 120° C. in oleum to give (7) and benzolactams (3, X=CO) being preferably hydrolyzed at 90° to 110° C. in dilute mineral acids, and the resulting nitro compounds (7) or (8) are finally reduced to give amino compounds of the structure (5) or (6), respectively. The reduction can be carried out catalytically (for example hydrogen/Raney nickel catalyst), by means of metal/acid or by means of other reducing agents customary for aromatic nitro groups.

The substitution or cyclization reaction leading to compounds of the structure (3) is carried out on the model of DE-A 1,670,759 at above 80° C., most advantageously between 90° and 105° C., and if necessary under pressure. The reaction medium used is primarily water; it is also possible, however, to use an organic, water-miscible solvent, for example alcohol, DMF or dimethyl sulphoxide, or a mixture of these with water. It is preferable to carry out the reaction in water under reflux conditions. The auxiliary base is required to deprotonate the OH group in (2) and to absorb the hydrogen halide H-Hal which is liberated in the course of the condensation reaction. The substitution reaction takes place in an intramolecular manner giving single substances.

The use of 20% strength oleum at 75°-90° C. has proved particularly suitable for the hydrolysis of the compounds (3, X=SO₂) and (4, X=SO₂).

The invention also relates to new 7-amino-1,4-benzoxazepin-5-ones of the structure (9)

which X=SO₂ and R=optionally substituted C₁-C₄-alkyl, C₂-C₄-alkenyl or C₂-C₄-alkinyl, which is characterized in that compounds of the structure (3) in which X=SO₂ and R=H are subjected to base-catalyzed alkylation with alkylating agents such as R-Hal or epoxides, such as, for example, chloroacetic acid or ethylene oxide, or with activated double bond systems, such as, for example, acrylonitrile or acrylic acid esters. The preferred reaction medium in this case is water and the reaction temperature is within the range from 50° to 110° C.

A process is also claimed for the preparation of β-phenoxyethylamines of the structure (10), such as are described, for example, in DOS (German Published Specification) 3,635,312

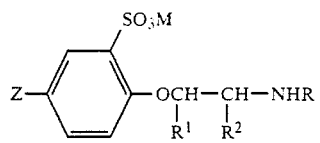

in which Z=NO₂ or NH₂,
which is characterized in that amidosulphonic acids of the structures (5) and (7) are hydrolyzed by means of dilute mineral acids, in particular hydrochloric acid or sulphuric acid, under reflux conditions or at elevated temperatures under pressure.

The use of the new, claimed compounds of the structures (1), (5), (6), (7), (8) and (9) is also claimed for the preparation of dyestuffs, especially of the compounds in which Z=NH₂, as diazo components in azo dyestuff chemistry or as condensation components for activated quinones, such as chloranil, for the synthesis of triphendioxazine dyestuffs.

For the preparation of triphendioxazine dyestuffs compounds of the formula (1) or (10) in which Z=NH₂ are subjected to a condensation reaction in a known manner with 1,4-benzoquinones to give dyestuff precursors of the formula (11)

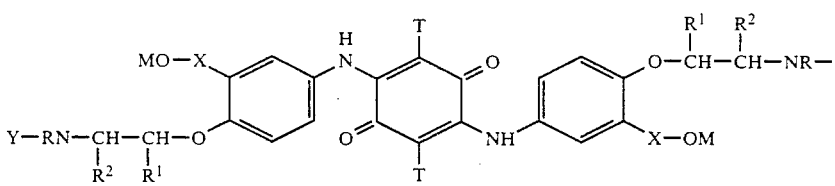

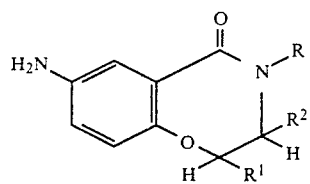

which are formed as intermediate products (4) having X=CO in the course of the process of preparation claimed, in particular 7-amino-2,3-dihydro-(5H)-1,4-benzoxazepin-5-one, 7-amino-4-methyl-2,3-dihydro-(5H)-1,4-benzoxazepin-5-one and 7-amino-4-(2'-hydroxyethyl)-2,3-dihydro-(5H)-1,4-benzoxazepin-5-one.

The invention also relates to a process for the preparation of intermediate products of the structure (3) in wherein
T=Cl, Br, CO₂CH₃,

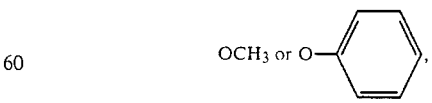

X=SO₂ or CO,
Y=H or SO₃M
and M, R, R¹ and R² have the meaning mentioned under formula (1),
and a cyclization to give triphendioxazine dyestuffs of the formula

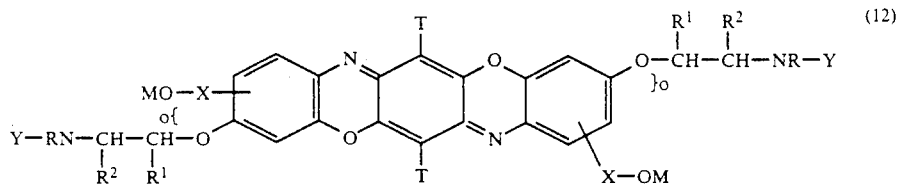

is then carried out, the X-OM radicals being in each case in one of the ortho-positions relative to the aminoethoxy radical. The cyclization can be effected, for example, by methods such as are described in German Offenlegungsschriften (German Published Specifications) 2,122,262, 2,124,080, 2,302,382, 2,344,781, 2,503,611 and 2,823,828 and in British Patent Specification 2,019,872. Dyestuffs of the formula (12) in which $Y=SO_3M$ can be hydrolyzed by means of dilute mineral acids to give dyestuffs in which $Y=H$.

Dye bases of the formula (12) in which $Y=H$ can also be reacted with reactive components of the structure Q-Hal (Q = a fiber-reactive radical and Hal = Cl, Br or F) to give fiber-reactive triphendioxazine dyestuffs, some of which are known, of the formula (12) in which $Y=Q$ wherein Q = a fiber-reactive radical, in particular those belonging to the triazine or pyrimidine series (see DE-A 3,635,312).

The following are examples of typical dyestuffs:

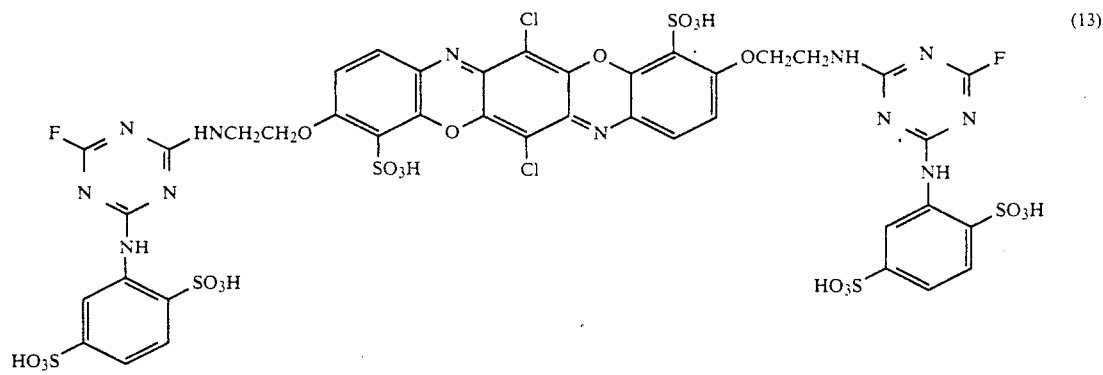

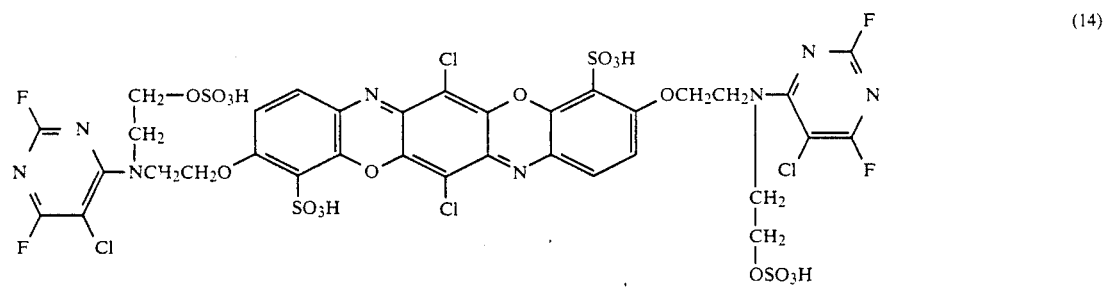

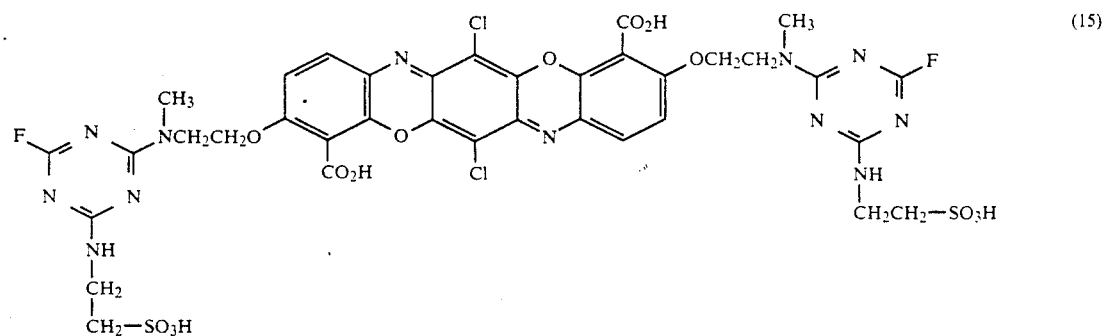

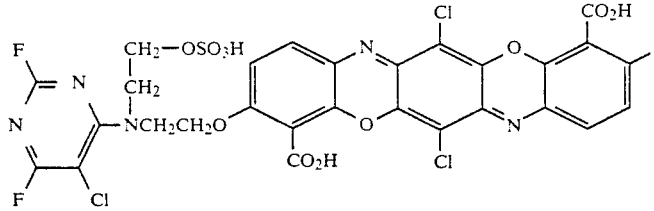
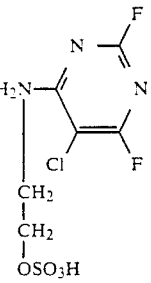

(16)

Dyestuffs (12) in which Y=SO₃H can also be prepared by subjecting activated 1,4-benzoquinones to a condensation reaction with amino compounds (4) by known methods (for example isopropanol/sodium acetate (60°–80° C.) to give dark olive dyestuff precursors of the structure (17)

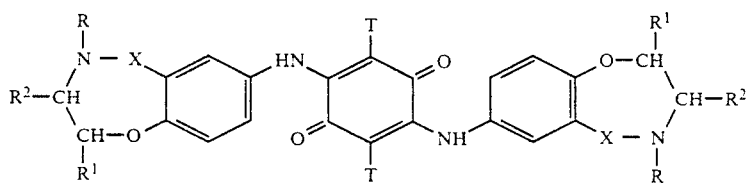

(17)

and then cyclizing the latter in oleum at 60°–120° C., preferably at 75°–85° C., with simultaneous opening of the benzosultam or benzolactam ring system, to give triphendioxazines. The invention relates to this new process and also to the new red dyestuffs or dyestuff intermediate products of the structure (12) in which Y=SO₃H.

Subjecting (17) to condensation in oleum at about 20°–40° C. gives dyestuffs of the following structure (18)

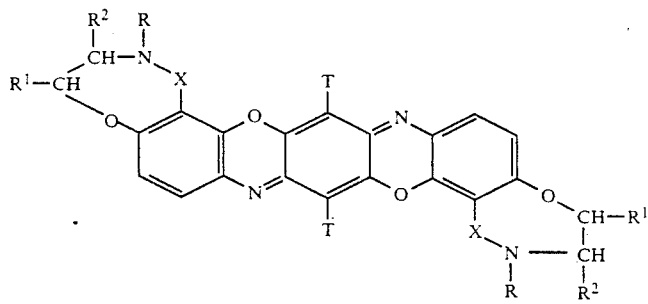

(18)

which are also a subject of the invention.

The dyestuffs (12) in which Y=SO₃H are particularly suitable for dyeing paper and leather.

Dyestuffs (12) in which X=CO and Y=a fiber-reactive group are new and are also a subject of the invention. These dyestuffs are suitable for dying cotton.

Dyestuffs (18) containing groups which impart solubility in water are preferentially suitable for dyeing paper and leather, while those which are free from groups imparting solubility in water are suitable for dyeing synthetic materials or polyesters.

EXAMPLE 1

244 g of 8-nitro-3,4-dihydro-(2H)-5,1,2-benzoxathiazine 1,1-dioxide, which is accessible by an intramolecular condensation reaction from 2-chloro-5-nitro-N-(2-hydroxyethyl)-benzenesulphonamide (DOS (German Published Specification) 1,670,759), are suspended in 600 ml of methanol and are reduced in the presence of 3 g of freshly prepared Raney nickel as catalyst by injecting three times the equimolar amount of hydrogen in an autoclave at 50° C. When the reduction is complete, the catalyst is removed from the hot reaction solution, from which the amino compound crystallizes out in fine flakes after cooling to 0° C. 205 g of 8-amino-3,4-dihydro-(2H)-5,1,2-benzoxathiazepine 1,1-dioxide of the formula

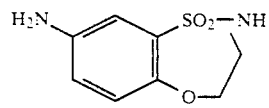

melting point 179° C. are obtained after filtering off with suction and drying.

¹H-NMR (D₆-DMSO): δ=3.36 (2H,t); 3.91 (2H,t); 5.30 (NH₂,s); 6.61 (1H,dd); 6.85 (1H,d); 6.94 (1H,d); 7.50 (NH,s) ppm.

The following amino compounds (Examples 2, 3 and 4) are accessible by reduction analogously:

EXAMPLE 2

8-Amino-2-methyl-3,4-dihydro-5,1,2-benzoxathiazepine 1,1-dioxide (melting point 148° C.)

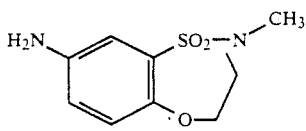

¹H-NMR (D₆-DMSO): δ=2.62 (3H,s); 3.57 (2H,t); 3.97 (2H,t); 5.34 (NH₂,s); 6.65 (1H,dd); 6.84–6.88 (2H,m) ppm.

EXAMPLE 3

8-Amino-2-(2-hydroxyethyl)-3,4-dihydro-5,1,2benzoxathiazepine 1,1-dioxide (melting point 141° C.)

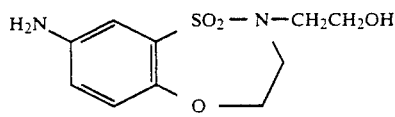

¹H-NMR (D₆-DMSO): δ=2.92 (2H,t); 3.53 (2H,m); 3.66 (2H,m); 3.99 (2H,m); 4.82 (OH,t); 5.36 (NH₂,s); 6.67 (1H;dd); 6.84–6.92 (2H ,m) ppm.

EXAMPLE 4

8-Amino-2-phenyl-3,4-dihydro-5,1,2-benzoxathiazepine 1,1-dioxide (melting point 189° C.)

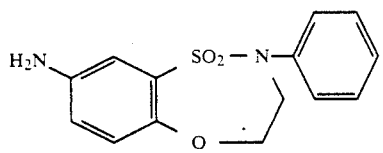

¹H-NMR (d₆-DMSO): δ=4.02 (2H,m); 4.10 (2H,m); 5.40 (NH₂,s); 6.74 (1H,dd); 6.89 (1H,d); 6.98 (1H,d); 7.11 (2H,d); 7.22–7.37 (3H,m) ppm.

The 8-nitro-2-(2-hydroxyethyl)-3,4-dihydro-5,1,2-benzoxathiazepine 1,1-dioxide required for the preparation of Example 3 is accessible by the following 2 methods of synthesis:

Route A 324.5 g of N,N-bis(2-hydroxy-ethyl)-2-chloro-5-nitrobenzenesulphonamide, prepared from 2-chloro-5-nitrobenzenesulphonyl chloride and diethanolamine, are heated under reflux conditions in 1 l of water with 56 g of solid potassium hydroxide. After a reaction time of 1 hour the reaction mixture is cooled and the precipitated product is isolated. 262 g of single-substance nitrobenzosultam are obtainted (melting point 124° C.).

Route B 122 g of 8-nitro-3,4-dihydro-(2H)-5,1,2-benzoxathiazepine 1,1-dioxide are dissolved in 300 ml of water by adding 20 g of sodium hydroxide. The solution is heated to 60° C. with stirring and approximately 30–35 g of ethylene oxide are passed in slowly under a protective atmosphere of N₂. When the metered addition is complete stirring is continued for 2 hours and the excess ethylene oxide is removed by passing in nitrogen. The reaction mixture is neutralized and cooled to 20° C. Isolation of the crystalline precipitate gives 129 g of an alkylation product which proves to be identical with the 8-nitro-2-(2-hydroxyethyl)-3,4-dihydro-5,1,2-benzoxathiazepine 1,1-dioxide isolated by route A.

EXAMPLE 5

260 g of N-(2-hydroxyethyl)-N-methyl-2-chloro-5-nitrobenzamide, which is prepared from 2-chloro-5-nitrobenzoyl chloride and 2-(methylamino)-ethanol, are heated to reflux temperature in 500 ml of water/500 ml of isopropanol. A solution of 65 g of potassium hydroxide in 250 ml of water is added dropwise in the course of one hour and the mixture is maintained at reflux temperature for a further 3 hours. The pH is lowered to 9, the reaction solution is cooled to 0° C. and the crystalline precipitate is filtered off with suction and dried. 174 g of 7-nitro-4-methyl-2,3-dihydro-1,4-benzoxazepin-5-one of melting point 116° C. are obtained.

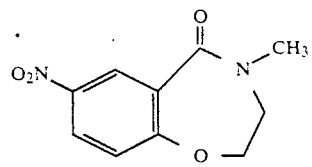

¹H-NMR (D₆-DMSO): δ=3.12 (3H,s); 3.71 (2H,m); 4.57 (2H,m); 7.17 (1H,d); 8.22 (1H,dd); 8.61 (1H,d)ppm.

EXAMPLE 6

144.5 g of N,N-bis(2-hydroxyethyl)-2-chloro-5-nitrobenzamide in 500 ml of water containing 28 g of potassium hydroxide are heated for 2 hours with reflux cooling. The mixture is cooled to 10° C. and the precipitated, single-substance product is filtered off with suction and dried. 84 g of 7-nitro-4-(2-hydroxyethyl)-2,3-dihydro-1,4-benzoxazepin-5-one of melting point 151° C. are obtained.

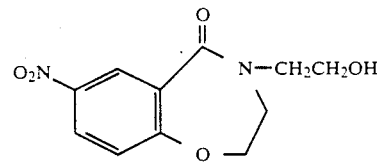

¹H-NMR (D₆)-DMSO); δ=3.67 (4H,m); 3.76 (2H,t); 4.58 (2H,t); 4.84 (OH,t); 7.18 (1H,d); 8.23 (1H,dd); 8.66 (1H,d) ppm.

EXAMPLE 7

111 g of the nitro compound obtained under Example 5 are suspended in 450 ml of methanol and are reduced, in the presence of 3 g of freshly prepared Raney nickel as catalyst, by injecting three times the equimolar amount of hydrogen in an autoclave at 50° C. When the reduction has been carried out the catalyst is separated off from the warm reaction solution. The solution is concentrated on a rotary evaporator. 91 g of dry 7-amino-4-methyl-2,3-dihydro-1,4-benzoxazepin-5-one of melting point 165° C. are isolated.

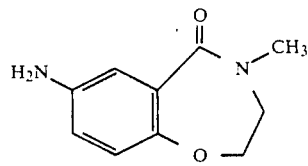

$^1$H-NMR (D$_6$-DMSO): δ=3.04 (3H,s); 3.40 (2H,t); 4.13 (2H,t); 5.05 (NH$_2$,s); 6.61 (1H,dd); 6.68 (1H,d); 6.74 (1H,d) ppm.

EXAMPLE 8

The nitro compound obtained under Example 6 is reduced in a manner similar to that under item 7 to give 7-amino-4-(2-hydroxyethyl)-2,3-dihydro-1,4-benzoxazepin-5-one of melting point 138° C.

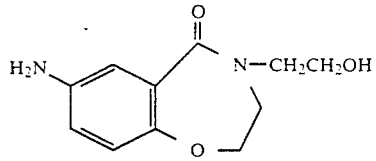

$^1$H-NMR (D$_6$-DMSO); δ=3.44 (2H,t); 3.53 (4H,m); 4.13 (2H,t); 4.80 (OH,t); 4.99 (NH$_2$,s); 6.60 (1H,dd); 6.69 (1H,d); 6.72 (1H,d) ppm.

EXAMPLE 9

352 g (approximately 1.5 mol) of the amino compounds obtained in Example 1 are introduced in portions into a stirred vessel containing 900 ml of 20% strength oleum. In the course of this, the temperature should not exceed 60° C. The mixture is then heated at 80° C. with stirring for 2 hours. It is allowed to cool and is discharged onto a mixture of 500 ml of water and a total of 3.5 kg of ice.

When the temperature has reached 10°-15° C. the crystalline precipitate is filtered off with suction, rinsed with 200 ml of water and dried. This gives 537 g of amidosulphonic acid of the structure (probably betaine structure)

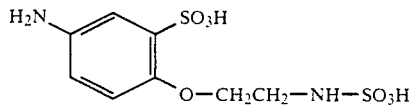

Determination of purity by means of sodium nitrite solution gives a value of 38.5 g=0.1 mol, corresponding to a yield of 93% of theory.

$^1$H-NMR (D$_2$O,NaOH): δ=3.36 (2H,t); 4.23 (2H,t); 6.91 (1H,dd); 6.98 (1H,d); 7.22 (1H,d) ppm.

C,H,N-analysis:
calc.: C 30.76; H 3.85; N 8.97; O 35.9; S 20.51%;
found: C 30.0 ; H 3.9; N 8.7; O 35.4; S 20.1%.

EXAMPLE 10

If the amino compound from Example 2 is subjected to a process analogous to that described under Example 9, the result is a substituted N-(β-phenoxyethyl)amidosulphonic acid of the structure

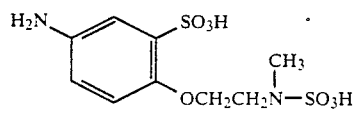

$^1$N=NMR (D$_2$O,NaOD): δ=2.84 (3H,s); 3.41 (2H,t); 4.25 (2H,t); 6.95 (1H,dd); 7.03 (1H,d); 7.25 (1H,d) ppm.

EXAMPLE 11

300 g (1.2 mol) of the 8-nitro-3,4-dihydro-(2H)-5,1,2-benzoxathiazepine 1,1-dioxide from Example 1, which is accessible by the method of DOS (German Published Specification) 1,670,759, are introduced in portions into a stirred vessel containing 800 ml of 20% strength oleum. In the course of this the temperature should not exceed 60° C. The mixture is then heated at 80°-83° C. for 1 hour. Since the starting compound can no longer be detected by chromatography, the reaction solution is cooled to 20° C. and discharged onto an ice water mixture. 48 g of sodium hydroxide are introduced in portions and stirring is continued for 1 hour. The crystalline precipitate is isolated and a small sample of it is dried. According to MR data and analysis the hydrolysis product has the structure

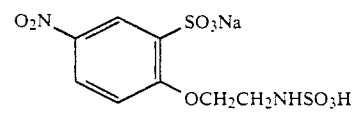

$^1$H-NMR (D$_{20}$,NaOD): δ=3.52 (2H,t); 4.48 (2H,t); 7.30 (1H,d); 8.35 (1H,dd); 8.57 (1H,d) ppm.

EXAMPLE 12

The remainder of the material isolated, the moist paste, from Example 11 is stirred into 800 ml of water and the pH of the mixture is adjusted to 8 by means of concentrated sodium hydroxide solution, with external cooling. After 5 g of Raney nickel have been added, hydrogen is injected into the autoclave at 25° C. A total of 3.2 mol of hydrogen are required for the reduction. In the course of this the reaction temperature rises to 50° C. When the absorption of hydrogen is complete, the mixture is cooled and the pressure in the apparatus is released. The catalyst is removed from the reaction solution by filtration. 200 ml of 48% strength sulphuric acid are added to the solution, in the course of which the reduction product crystallizes out slowly. 340 g of an amino compound which proves to be identical with the amidosulphonic acid of Example 9 are obtained after isolation and drying. The content of amino compound is 95.8% in respect of a molecular weight of 334 (mono-Na salt), that is to say the yield for the two reaction stages is 82% of theory.

EXAMPLE 13

250 g of the amidosulphonic acid derivative from Example 9 (81% strength) are boiled under reflux in 2.2 l of 10% strength hydrochloric acid for about 6 hours until a sample no longer shows educt when chromatographed. After being stirred under cold conditions overnight, the product of the formula

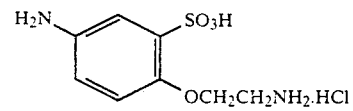

is precipitated in the form of needles, which are filtered off with suction, covered with cold 10% strength hydrochloric acid and dried. For analysis, it is preferable to wash the product with acetone until it is free from hydrochloric acid and to dry it. This gives 149.8 g of the hydrochloride (86% of theory), which proves to be identical with a sample synthesized by a different route (as specified in DOS (German Published Specification) 3,635,312).

HCl calculated 13.59%; HCl found 13.63%.

EXAMPLE 14

46 g of the aminobenzolactam from Example 7 are heated under reflux in 290 g of 60% strength sulphuric acid for approximately 36 hours. The reaction solution is cooled and diluted with 250 ml of water. 160 g of calcium carbonate are introduced slowly until the pH has reached a value of about 2. The temperature meanwhile is kept at 20°–25° C. by adding ice. The precipitated calcium sulphate is removed and the resulting solution is neutralized with dilute sodium hydroxide solution and concentrated until crystallization begins. For further use, however, it is more advantageous after neutralization to react the solution of the compound of the formula

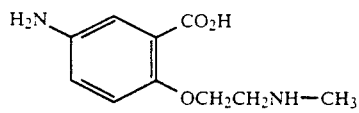

with suitable reactants, such as, for example, chloranil, without further treatment.

EXAMPLE 15

21.8 g of the aminobenzolactam from Example 8 are boiled under reflux at 110° C. in 66 ml of 20% strength hydrochloric acid for 8 hours until the educt can no longer be detected by chromatography. Cooling gives a water-white solution which, after being concentrated in vacuo, suddenly deposits a thick mash of crystals which, after being filtered off with suction, can be dried in a circulating air drying cabinet. 30.3 g are isolated; according to argentometric determination of Cl, the product proves to be the bishydrochloride of 5-amino-2-[2-(2-hydroxyethylamino)ethoxy]benzoic acid of the structure

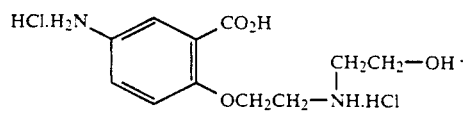

HCl calculated 23.3%; HCl found 23.4% .

$^1$H-NMR(D$_6$-DMSO): δ=3.16 (2H,m); 3.37 (2H,m); 3.68 (2H,t); 4.41 (2H,t); 7.28 (1H,d); 7.55 (1H,dd); 9.13 (2H, broad s); 10.3–11.8 (approx. 2H) ppm.

EXAMPLE 16

44 g of 8-amino-3,4-dihydro-(2H)-5,1,2-benzoxathiazepine 1,1-dioxide (Example 1), 25.1 g of chloranil (=2,3,5,6-tetrachloro-1,4-benzoquinone) and 31 g of anhydrous sodium acetate are heated in 500 ml of isopropanol for 5 hours with reflux cooling. The mixture is cooled and the product filtered off with suction. The brown-olive material isolated is washed with 50 ml of acetone and with three times 200 ml of water and is then dried. This gives 60.8 g of the bis-condensation product of the structure

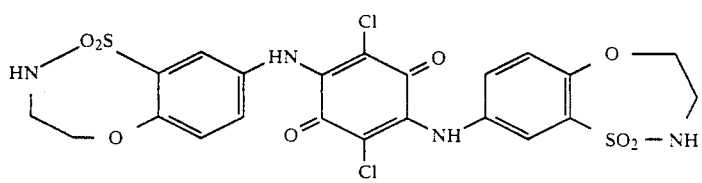

30 g of this sparingly soluble bis-condensation product are introduced in portions into 150 ml of 20% strength oleum at 30°–40° C. The mixture is heated with stirring at 80°–85° C. for 3 hours. After being cooled, the reaction solution is then discharged onto ice and the dark red precipitate is filtered off with suction. After isolation, the paste is neutralized by being stirred into 300 ml of water and the pH of the mixture is adjusted to 6.5 with dilute sodium hydroxide solution. After 30 g of sodium chloride and 45 kg of potassium chloride have been added, the mixture is stirred for 1 hour and the product is then again isolated by filtration. 26.1 g of a dark red-brown dyestuff powder which has the structure

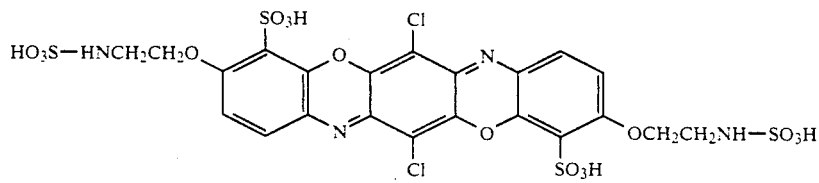

are obtained after drying. The new product can be employed, for example, as an ink jet dyestuff and then gives a light-fast magenta (λmax.=540 nm (H$_2$O)) on paper.

We claim:
1. A β-phenoxyethylamine of the formula

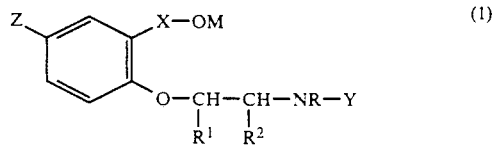

wherein
Z is NH$_2$ or NO$_2$,
M is H or an alkali metal cation, alkaline earth metal cation or ammonium cation,
R is H or a C$_1$–C$_4$-alkyl, C$_2$–C$_4$-alkenyl or C$_2$–C$_4$-alkinyl radical each of which is optionally substituted by OH, Cl, Br, CN, CO$_2$H, CO$_2$CH$_3$, CO$_2$C$_2$H$_5$, CONH$_2$, CON(CH$_3$)$_2$, SO$_3$H, OSO$_3$H or C$_1$–C$_4$-alkoxy, or a phenyl or benzyl radical each of which is optionally substituted by halogen, $C_1$-$C_4$-alkyl, $CO_2H$ or $SO_3H$, $R^1$ and $R^2$ each independently is H, $C_1$-$C_4$-alkyl, phenyl or benzyl, or together they complete a cycloaliphatic ring, X is $SO_2$ and Y is $SO_3H$.

2. An amine according to claim 1, wherein
R is $C_1$-$C_4$-alkyl, $CH_2CH_2OH$, $CH_2COOH$ or $CH_2CH_2OSO_3H$, and
$R^1$ and $R^2$ are H.

* * * * *